(12) United States Patent
Burgoyne

(10) Patent No.: US 6,291,179 B1
(45) Date of Patent: Sep. 18, 2001

(54) PRODUCT AND METHOD FOR SEPARATION OF A SAMPLE CONTAINING MULTIPLE SOURCES OF GENETIC MATERIAL USING A SOLID MEDIUM

(75) Inventor: Leigh Alexander Burgoyne, Mitcham (AU)

(73) Assignee: Whatman PLC, Kent (GB)

( * ) Notice: Subject to any disclaimer, the term of this patent is extended or adjusted under 35 U.S.C. 154(b) by 0 days.

(21) Appl. No.: 09/394,008

(22) Filed: Sep. 10, 1999

Related U.S. Application Data

(60) Provisional application No. 60/099,715, filed on Sep. 10, 1998.

(51) Int. Cl.[7] .............................. C12Q 1/68; C12P 19/34; A61K 9/14; A61K 9/16; C12N 11/02
(52) U.S. Cl. ................... 435/6; 435/91.5; 435/91.51; 435/91.1; 435/91.2; 435/177; 536/23.1; 536/25.4; 424/488; 424/484; 424/486; 424/489; 424/497
(58) Field of Search .................... 435/6, 91, 91.2, 435/91.51, 91.5, 7.1, 7.2, 7.9, 810, 177; 422/61; 536/25.4, 23.1; 424/488, 484, 489, 486, 497

(56) References Cited

U.S. PATENT DOCUMENTS

| | | | | |
|---|---|---|---|---|
| 5,234,809 | * | 8/1993 | Boom et al. | 435/91 |
| 5,496,562 | * | 3/1996 | Burgoyne | 424/488 |
| 5,637,687 | * | 6/1997 | Wiggins | 536/25.4 |
| 5,939,264 | * | 8/1999 | Rothschild et al. | 435/6 |

OTHER PUBLICATIONS

Huynh et al. Sequential Elution of Denatured proteins, hydrolyzed RNA and Plasmid DNA of bacterial lysates absorbed onto Stached DEAE cellulose memebranes. Analytical Biochemistry. vol. 211, pp. 61–65, Dec. 1993.*

* cited by examiner

Primary Examiner—Stephanie W. Zitomer
Assistant Examiner—Cynthia B. Wilder
(74) Attorney, Agent, or Firm—Kohn & Associates

(57) ABSTRACT

The present invention is directed to products and methods for storing, separating or analyzing a sample of genetic material. The invention is particularly suited for the separation of a selected genetic material from a sample containing genetic material from multiple sources.

20 Claims, No Drawings

PRODUCT AND METHOD FOR SEPARATION OF A SAMPLE CONTAINING MULTIPLE SOURCES OF GENETIC MATERIAL USING A SOLID MEDIUM

This application claims benefit of Provisional application Ser. No. 60/099,715. filed Sep. 10, 1998.

FIELD OF THE INVENTION

The present invention is directed to the storage, separation and analysis of genetic material. The invention is particularly suited for separating a genetic material from a sample containing multiple sources of a genetic material using a solid medium.

BACKGROUND OF THE INVENTION

The purification of genetic material from a crude sample for subsequent analysis can be laborious. Inadequate isolation of the genetic material from hemoglobin, proteins or other substance often associated with the generic material in a crude sample can inhibit or interfere with some analytical procedures such as, for example, polymerase chain reaction ("PCR"). Moreover, if the crude sample includes genetic material from multiple sources confusion of the genetic material analyzed can result.

Crude samples having multiple sources of genetic material include, for example, blood, feces, tissue fluids, plasmid containing bacteria, etc. The use of bacteria for propagation of plasmids is common in the study of genomics, analytic molecular biology, preparation molecular biology, etc. Methods for propagating plasmid containing bacteria are known. Common methods for storage of bacteria containing plasmids prior to analysis of the genetic material of the plasmid include, for example, filter paper, plastic, ceramic, semi-conductor, metal, etc.

Recently, new devices and methods for storage and purification of genetic material which are treated to protect the genetic material from degradation during storage and prior to analysis have become commercially available. Examples of such devices include products under the trade name FTA® available from Fitzco, Inc., Plymouth, Minn. Other examples are disclosed in U.S. Pat. Nos. 5,807,527; 5,756,126; and 5,496,562 and co-pending U.S. application Ser. No. 08/574,888. The disclosures of each of these patents and patent applications are incorporated herein by reference. Another example of a related product is IsoCode® available from Schleicher & Schuell, Keene, New Hampshire.

Purification and analysis of genetic material using a solid medium, such as those disclosed above, provide many advantages over wet storage methods. However, while these devices are suitable for storage and processing of genetic material, often times the genetic material stored in the form of a crude sample and may include genetic material derived from two or more different sources. For example, in the case of a bacterium containing a plasmid, genetic material from both the bacterium and plasmid are present. Thus, while a single sample may include genetic material from multiple sources, it is often advantageous to be able to distinguish the source of any particular piece of genetic material when the sample is analyzed.

Accordingly, there is a continuing need for products and methods which provide for purifying or separating a particular genetic material from a crude sample, including a sample containing genetic material from multiple sources.

SUMMARY OF THE INVENTION

The present application claims priority to U.S. Provisional Patent Application Ser. No. 60/099,715, filed Sep. 10, 1998, the entire disclosure of which is incorporated herein by reference.

The present invention is directed products and methods for purifying or separating a genetic material from a crude sample applied to a solid medium. In some embodiments, the invention provides for separating a selected genetic material from a sample containing genetic material from multiple sources.

It will be appreciated that throughout the specification, guidance may be provided through lists of examples. In each instance, the recited lists serve only as a representative group. It is not meant, however, that the lists are exclusive.

According to the invention, a sample of genetic material can be stored on a solid medium as described below. Once applied to the solid medium, non-genetic material typically associated with a crude sample, for example, proteins, fats, etc., can be removed from the dry solid medium using a cleaning solution. The dry solid medium can then be rinsed using a rinsing solution and the genetic sample analyzed in situ. Alternatively, the genetic material can be eluted from the solid medium and analyzed away from the solid medium.

In some embodiments, the invention further provides for purifying and removing a selected genetic material from a sample including genetic material from more than one source. According to this embodiment, the genetic material remaining on the solid medium can be further analyzed in situ, or, alternatively, the genetic material removed from the solid medium can further be analyzed away from the solid medium.

DETAILED DESCRIPTION OF THE INVENTION

The present invention is directed to products and methods which provide for separating genetic material derived from a crude sample that may contain genetic material from more than one source.

As used herein, the term "genetic material" includes a nucleotide sequence comprising two or more nucleotide bases including, for example, DNA, RNA, cDNA, oligonucleotides, entire genes, partial genes, entire genomes, etc. A "crude sample" refers to a sample of genetic material including components typically associated with the genetic material in vivo (e.g., proteins, fats, etc.) and includes, for example, a buccal swab, blood, serum, plasma, semen, feces, urine, cerebral spinal fluid, synovial fluid lymphatic fluid, etc. A "crude sample" also includes bacterial cultures, viral suspensions, etc. A "source" from which the genetic material is derived includes, for example, any type of eukaryotic or prokaryotic cell, viruses, plasmids, phages, archeobacteriae, plastids, cosmids, viroids, tissue fluids (blood, cerebrospinal fluid, lymphatic fluid, saliva, urine, etc.), etc. In one embodiment, the products and methods of the invention are particularly suited for purifying plasmid genetic material and separating genetic material of plasmids from bacteria containing the plasmids.

According to the invention, a sample containing genetic material can be applied to and stored on a medium comprising a support matrix such as paper (cellulose, nitrocellulose, etc.), plastic, ceramic, semi-conductor, metal, or other porous material or micro-indented surface or surface equipped with micropoles or microtrabeculae. In addition, the methods of the invention may also be used on genetic samples applied to and stored on a semi-solid matrix such as agar gel, agarose gel, polyacrylamide gel, etc.

The storage medium may also include one or more components which protect the stored genetic material from damage or degradation, denature proteins or which are useful for analysis of the stored genetic material. Examples of some such matrices are disclosed in U.S. Pat. Nos. 5,939,259; 5,807,527; 5,756,126; and 5,496,562; and co-pending U.S. Ser. No. 08/574,888.

As used herein, "analysis" of the genetic material includes methods used in the art for analyzing DNA or RNA such as sequencing, amplifying, hybridizing, probing, endonuclease restriction, ligation cloning, preparation for mass spectroscopy or irradiation, or any other procedure that is performed to obtain information about the genetic material. The genetic material can be analyzed immediately after taking the sample or stored for analysis at a later time.

According to the invention, some or all of the analysis to be performed on a particular source of genetic material can be analyzed in situ (i.e., on the medium) while source(s) not to be analyzed are removed from the medium prior to analysis. Alternatively, the genetic material to be analyzed can be removed from the medium, for example, the sources of genetic material which are not to be analyzed can remain on the medium and the genetic material to be analyzed removed from the medium prior to analysis. Thus, to analyze a particular source of genetic material from a multiple source sample, the methods herein described provide for selective removal from the solid medium of either the genetic material to be analyzed or the genetic material (and/or associated non-genetic material) not being analyzed.

In one embodiment, a sample of genetic material can include the genetic material of a bacterium (e.g., DNA and/or RNA) and the genetic material of a plasmid (e.g., DNA) that is contained within the bacteria. In one example of this embodiment, a wet sample of the bacteria containing the plasmid can be applied to the medium and permitted to dry. After drying, and typically prior to analysis of the genetic material, the genetic material of the bacteria and plasmid are separated.

Either the bacterial genetic material or the plasmid genetic material can be removed from the medium and the genetic material remaining on the medium analyzed in situ and/or the genetic material removed from the medium analyzed away from the medium. In one example, the plasmid genetic material can be removed from the medium and the bacterial genetic material left on the medium. If it is desired to analyze the genetic material of the plasmid, the plasmid can be eluted into an eluting solution from which further analysis of the plasmid genetic material can be performed. Alternatively, if it is desired to analyze the genetic material of the bacteria, once the plasmid genetic material is removed from the medium, the bacterial genetic material can be analyzed in situ on the medium.

According to the foregoing example, to separate the plasmid genetic material from the bacterial genetic material, a cleaning solution can be applied to remove components of the crude sample which are present on the medium and which can interfere with, or are not necessary for, analysis of the genetic material. The cleaning solution can be followed by a rinsing solution. Subsequently, an eluting solution can be applied to remove the genetic material of the source(s) selected to be removed without substantially removing the genetic material selected to remain on the medium.

As used herein, a "cleaning solution" provides for removal of non-genetic material. Non-genetic material includes sample constituents such as proteins, fats, cellular debris, bacterial techoic acids, plant tannins, other secondary plant products or components of the medium such as protein denaturing agents (e.g., detergents; urea; guanidium salts, such as guanidine thiocyanate, guanidine isothiocyanate, guanidine hydrochloride; sodium iodide; chelating agents such as EDTA; free radical traps such as uric acid (or a urate salt), guanidine thiocyanate, etc.; protective agents; etc. In some embodiments, such as during plasmid preparation, the cleaning solution can also provide for RNA removal, for example, by selective RNA destruction in alkaline solution.

In one embodiment, the cleaning solution can be a "partial aqueous, alkaline solution" (PAA). As used herein a "PAA" solution includes a water miscible solvent (e.g., alcohol, methanol, ethanol, propanol, butanol, their isometric diols or polyols, etc.; acetone, etc.) in combination with a source of high pH. When the water miscible solvent is the alcohol ethanol, concentrations of ethanol can be about 30 to 90%, typically about 45% to 70%. Generally, a "high pH" source provides a PAA solution pH of about 9.0 to 13, preferably about 11. Examples of sources of high pH include: NaOH, KOH, LiOH, quaternary nitrogen base hydroxide, tertiary, secondary or primary amines, etc. A preferred PAA can function as a denaturing agent as well as a solvent for solubilizing and removing protein from the medium.

As an alternative to PAA, detergent or chaotropic alcohol solutions, for example, an anionic detergent in combination with an alcohol can also be used as a cleaning solution. However, some of the advantageous features of a PAA, such as RNA destruction could be lost. Additional less preferred cleaning solutions include, for example, certain chaotropic agents in alcohol and phenol solutions. Suitable phenol solutions are disclosed in U.S. Pat. No. 5,756,126 and co-pending Ser. No. 08/574,888, the entire disclosures of which are incorporated herein by reference.

In an example of removing plasmid DNA and leaving bacterial DNA on the solid medium, complementary cross linking and relative size of the bacterial DNA facilitates retention to the solid medium. However, it is also foreseen that covalently attaching DNA sequences or peptide NA (PNA) sequences to the medium can be utilized to enhance the differential binding of one source of genetic material over another. Also, enhanced binding of one type of genetic material versus another can be provided by incorporating some reverse-phase characteristics to the medium. Such reverse-phase characteristics can be provided, for example, by slightly siliconizing a hydrophobic medium or attaching benzyl, napthyl or similar groups.

As used herein, a "rinsing solution" provides for removing non-genetic material remaining after removal of the cleaning solution as well as removing or neutralizing components of the cleaning solution. Generally, a rinsing solution can comprise the water miscible solvent of the cleaning solution. Thus, this includes alcohols such as methanol, ethanol, propanol, butanol, their isometric diols or polyols, etc.; acetone, etc. The rinsing solution can either be unbuffered or contain a buffer at neutral pH or slightly below pH 7.0. When present, a buffer aids in the neutralization of the alkali of the cleaning solution. The composition of the buffer is selected so that traces of the buffer that are carried through the preparation procedure are compatible with the subsequent application of the genetic material. For example, Tris and EDTA buffers are suitable if the final usage of the DNA is to be as a solution in EDTA containing buffers. However, one preferred buffer for general usage is ammonium acetate at concentrations between 5 mM and 100 mM, with or without a small amount of EDTA, for example, 0.1 mM. EDTA.

As used herein, an "eluting solution" is a solution that selectively removes the genetic material of one or more sources from the medium without substantially removing other sources. As used herein, "substantially" means that while the separation of the source(s) of genetic material selected to be removed and the source(s) selected to remain may not be perfect, the separation is sufficient to provide reliable analytic results of the genetic material to be analyzed. In a typical embodiment, the eluting solution is a saline eluting solution. Examples of suitable saline eluting solutions include ethylenediaminetetraacetic acid (EDTA), sodium citrate, acetate, Tris EDTA buffer (TE), ammonium acetate (e.g., 10 mM concentration), carbonate salts, bicarbonates (e.g., 10 mM concentration), etc. Tris EDTA buffer can be prepared by combining 10 mM Tris free base and 1 mM EDTA, and adjusting to pH 8 with HCl.

In one embodiment, the eluting solution can also contain ethanol acetone, methanol, propanol, butanol, etc. and their isomeric diols and polyols. The foregoing components can be present in lower levels than contained in the cleaning and/or rinsing solution, for example, 0% to 55% v/v. The preferred concentration of these components for non-selective extraction is, however, 0%.

After application of the eluting solution, the genetic material to be eluted from the medium can be eluted using such methods as centrifugation, vacuum, diffusion, electrophoresis and electro-osmosis.

The invention will be further described by reference to the following Examples. It should be understood that the Examples are not intended to limit the invention, but rather only to clarify operation of the invention.

EXAMPLES

Example 1

The method of this Example is advantageous for use when a small amount of plasmids are needed from large numbers of samples as, for example, when sequencing large numbers of plasmids. According to this Example, handling is minimized while time consumed by the procedure may be increased. All operations were at room temperature. (i.e., about 20° C.)

1 ml cultures of Escherichia coli (*E. coli*) strain DH10B containing pBC-SR plasmids were centrifuged for 5 minutes at 150,000 rpm. Each centrifuged pellet was taken up in 10 $\mu$l of water with a trace of bromophenol blue as an indicator of position, and then deposited on a piece of FTA® paper (available from Fitzco, Inc., Plymouth, Minn.) as a blue spot, allowed to dry and stored dry.

3×2 mm punches were taken from the colored plasmid spots on FTA® paper and placed into a blank tube. 1 ml of a cleaning solution of 0.1 M NaOH in 52.5% ethanol v/v was placed on the discs and then gently agitated to wash and hydrolyze for 40 minutes.

The cleaning solution was aspirated and a rinsing solution of 1.0 ml, 95% ethanol was added and agitated gently for 5 minutes at room temperature and then dried.

An eluting solution of 15 $\mu$l of 5 mM tris EDTA at pH 8.3 was applied to the disc and left overnight at 4° C. for the plasmid to elute. The eluting solution and eluant were removed from the tube. The product was electrophoresed on 1% agarose gel and visualized with ethidium bromide by standard technology. Faint but clear plasmid bands were observed with the expected mobility and with a brightness indicative of a satisfactory yield for the very small amount of starting material.

Example 2

This Example is advantageous for use when larger amounts of plasmid are needed, as for example when restriction mapping is to be performed. This Example uses centrifugal stripping to remove solutions from the paper instead of long periods of diffusion. Centrifugal stripping was at 2500 rpm and each stripping took an additional 5 minutes for the centrifugation. All operations were at room temperature (20° C.).

One spot of plasmid-containing *E. coli* that had been held for 6 days on FTA® paper as described in Example 1 was cut into 4 sections and one of the four sections, of approximately 4 mm square, was placed in an apparatus suitable for centrifugal stripping (e.g., a test tube with a hole in the bottom, inside another tube that collects the eluate) and the centrifugal eluates collected. Other suitable systems for stripping will be apparent to those skilled in the art.

150 $\mu$l of cleaning solution was applied 4 times at about 2.5 minutes per time. The cleaning solution comprised 62% alcohol and the remainder being water with an overall composition for the water plus alcohol of 0.1M NaOH. The section was rinsed two times for about 2 minutes each time using 150 $\mu$l of 95% alcohol water. The elapsed time of washing and rinsing, inclusive of centrifugation time, is approximately 1 hour. An eluting solution of 15 $\mu$l TE buffer was applied 1 minute followed by centrifugation.

The observed product in the TE buffer was electrophoresed on 1% agarose gel and visualized with ethidium bromide by standard technology. Bands of the expected size classes were observed with intensities appropriate for the amount of *E. coli* they were derived from.

Example 3

The present Example describes purification of a sample of blood DNA stored on a solid medium and subsequent removal of the DNA from the solid medium.

A 6 mm disc of dry blood (approximately 16 $\mu$l) was previously applied to FTA® paper available from Fitzco, Inc., Plymouth, Minn. The sample was washed two times with a cleaning solution of 1.0 ml of 0.3 M $NaCO_3$ at room temperature. The first wash was for 30 minutes followed by aspiration and the second wash for 20 minutes followed by aspiration and spinning. The sample was then washed with 50 mM acetic acid for approximately 2 minutes followed by spin stripping and heating dry for 10 minutes at 99°. Subsequently, 20 $\mu$l of 15 Mm $NaCO_3$ was applied to the sample at 99° C. for 2–2.5 minutes and then eluted with 2 aliquots of 50 $\mu$l of water. The eluant was frozen in 10 $\mu$l lots and subsequently analyzed successfully by polymerase chain reaction (PCR).

Example 4

A 6 mm disc was punched out of a blood sample stored on FTA® paper. The non-genetic material (particularly proteins and components of the FTA® paper) were cleaned by gentle agitation of the disc with 2 washes of 500 $\mu$l of 0.3 M $Na_2CO_3$. The first wash was 25 minutes (long enough to imbibe the blood). The second wash was for 10 minutes and the sample was subsequently centrifugally stripped.

The cleaning solution was removed by washing and spin stripping with 3 aliquots of 200 $\mu$l each of water. The sample was exposed to the water for 1 to 2 minutes between each washing. The blood color of the disc was substantially gone at this point.

2 mM boric acid was applied in an amount sufficient to soak each disc (approximately 14 $\mu$l) and placed in a laboratory autoclave at 121–124° C. The autoclave was set for wet cycle at an approximate pressure of 140 kpa. The samples can be autoclaved for approximately 5 to 15 minutes, typically about 7 minutes. After the autoclave was at room temperature and pressure, 100 µl of water was applied to each disc and the DNA was eluted with two 100 µl aliquots of water. Each aliquot was removed from the sample by spin stripping. The collected DNA was subsequently analyzed by PCR.

In using this procedure, care should be taken not to damage the DNA by excessive autoclaving times. Once the DNA is eluted, it should be maintained chilled, protected by the addition of TE or similar alkaline buffer with a small amount of EDTA, or used immediately.

From the foregoing detailed description and examples, it will be evident that modifications and variations can be made to the invention without departing from the spirit or scope of the invention. Therefore, it is intended that all modifications and verifications not departing from the spirit of the invention come within the scope of the claims and their equivalents.

What is claimed is:

1. A method for separating a selected genetic material from a crude sample containing genetic material applied to a solid medium, the method consisting of:

applying a cleaning solution of a water miscible solvent mixed with a source of pH in the range of 9.0 to 13.0 to the sample of genetic material on the solid medium the solution destroying RNA in the sample;

applying an eluting solution to the sample of genetic material on the solid medium; and collecting the selected genetic material in the eluting solution.

2. The method according to claim 1 wherein the selected genetic material is further analyzed by polymerase chain reaction.

3. The method according to claim 1 wherein the selected genetic material is further analyzed by restriction fragment length polymorphism.

4. The method according to claim 1 wherein genetic material not removed from the solid medium is analyzed.

5. The method according to claim 4 wherein the genetic material not removed from the solid medium is analyzed by polymerase chain reaction in situ.

6. The method according to claim 1 wherein the solid medium comprises:

a solid matrix; and a protein denaturing agent.

7. The method according to claim 6 further comprising a free radical trap.

8. The method according to claim 7 wherein the protein denaturing agent is a detergent and the free radical trap is uric acid or a urate salt.

9. The method according to claim 7 wherein the protein denaturing agent and free radical trap is guanidium thiocyanate.

10. The method according to claim 7 wherein the protein denaturing agent is guanidine hydrochloride and the free radical trap is uric acid or a urate salt.

11. The method according to claim 6 wherein the protein denaturing agent is a guanidium salt.

12. The method according to claim 7 wherein the free radical trap is guanidine thiocyanate.

13. The method according to claim 7 wherein the protein denaturing agent is urea and the free radical trap is uric acid or a urate salt.

14. The method according to claim 1 wherein the crude sample includes genetic material from multiple sources.

15. A kit for separating a selected genetic material from a sample, the kit consisting of:

a solid medium;

a cleaning solution of a water miscible solvent mixed with a source of pH in the range of 9.0 to 13.0, the solution destroying RNA in the sample; and an eluting solution.

16. The kit according to claim 15 wherein the cleaning solution comprises ethanol and sodium hydroxide.

17. The kit according to claim 15 wherein the eluting solution is a saline eluting solution.

18. The kit according to claim 17 wherein the saline solution comprises 10 mM ammonium acetate.

19. The kit according to claim 17 wherein the saline solution comprises 10 mM ammonium bicarbonate.

20. A method for separating genetic material of a plasmid from genetic material of a bacteria applied as a sample to a solid medium, the method consisting of:

applying a sample including the bacteria containing the plasmid to a solid medium;

applying a cleaning solution of a water miscible solvent mixed with a source of pH in the range of 9.0 to 13.0 to the sample on the solid medium the solution destroying RNA in the sample;

applying a rinsing solution to the sample on the solid medium; applying an eluting solution to the sample on the solid medium; and collecting the genetic material of a selected one of the bacteria and plasmid in the eluting solution.

* * * * *